United States Patent
Guang et al.

(10) Patent No.: US 8,394,776 B2
(45) Date of Patent: Mar. 12, 2013

(54) USE OF URSOLIC ACID SAPONIN, OLEANOLIC ACID SAPONIN IN PREPARATION OF INCREASING LEUCOCYTES AND/OR PLATELET MEDICINE

(75) Inventors: Bing Guang, Sichuan (CN); Junjian Liu, Sichuan (CN); Guangxin Dong, Sichuan (CN); Xiangyang Peng, Sichuan (CN); Xiaoxia Gong, Sichuan (CN); Zhen Huang, Sichuan (CN); Meirong Zhou, Sichuan (CN); Wei Zhan, Sichuan (CN); Jufang Yan, Sichuan (CN); Yu Huang, Sichuan (CN); Dongguang Qin, Sichuan (CN); Jianxin Ji, Sichuan (CN); Bogang Li, Sichuan (CN)

(73) Assignee: Chengdu Di'Ao Jiuhong Pharmaceutical Factor, Sichuan (CN)

( * ) Notice: Subject to any disclaimer, the term of this patent is extended or adjusted under 35 U.S.C. 154(b) by 440 days.

(21) Appl. No.: 12/523,314

(22) PCT Filed: Jan. 16, 2008

(86) PCT No.: PCT/CN2008/000107
§ 371 (c)(1),
(2), (4) Date: Mar. 26, 2010

(87) PCT Pub. No.: WO2008/086739
PCT Pub. Date: Jul. 24, 2008

(65) Prior Publication Data
US 2010/0197898 A1    Aug. 5, 2010

(30) Foreign Application Priority Data

Jan. 16, 2007 (CN) .......................... 2007 1 0048277
Jan. 16, 2007 (CN) .......................... 2007 1 0048278

(51) Int. Cl.
*A01N 43/04* (2006.01)
*A61K 31/70* (2006.01)

(52) U.S. Cl. ......................................... 514/33
(58) Field of Classification Search .......... None
See application file for complete search history.

(56) References Cited

FOREIGN PATENT DOCUMENTS

| CN | 1210864 | 3/1999 |
|---|---|---|
| CN | 1355172 | 6/2002 |
| CN | 1446818 | 10/2003 |
| CN | 1472220 | 2/2004 |
| CN | 1593436 | 3/2005 |
| CN | 1628679 | 6/2005 |
| CN | 1682748 | 10/2005 |
| CN | 1788758 | 6/2006 |
| JP | 2000-256391 | 9/2000 |
| JP | 2006-206468 | 8/2006 |
| KR | 2006/112932 | 11/2006 |
| WO | 03/045410 | 6/2003 |

OTHER PUBLICATIONS

Vippagunta et al. Advanced Drug Delivery Reviews 48 (2001) 3-26.*
Matsuda et al. Life Sciences, vol. 63.No. 17, pp. PL 245-250, 1998.*
Gao. CN 1788758 A, Jun. 21, 2006, machine translation.*

* cited by examiner

*Primary Examiner* — Layla Bland
(74) *Attorney, Agent, or Firm* — Occhiuti Rohlicek & Tsao LLP

(57) ABSTRACT

The invention provides the use of ursolic acid saponin and oleanolic acid saponin of formula (I) in preparing medicaments for increasing leucocytes and/or platelets. The invention also provides a pharmaceutical composition containing the same compound. The invention utilizes the cheap and accessible ursolic acid and oleanolic acid which are widely present in natural plants as raw materials, introduces monosaccharyls or oligosaccharyls by structural modification. It is proved by pharmacological tests that the compound of formula (I) have an activity of obviously increasing leucocytes and/or platelets.

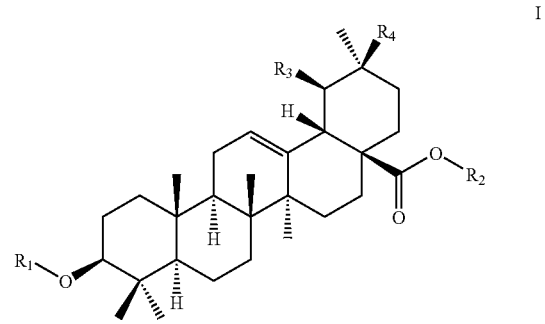

2 Claims, No Drawings

USE OF URSOLIC ACID SAPONIN, OLEANOLIC ACID SAPONIN IN PREPARATION OF INCREASING LEUCOCYTES AND/OR PLATELET MEDICINE

CROSS-REFERENCE TO RELATED APPLICATIONS

This application is the National Stage of International Application No. PCT/CN2008/000107, filed on Jan. 16, 2008, which claims the benefit of Chinese Application Serial No. 200710048277.1, filed on Jan. 16, 2007 and Chinese Application Serial No. 200710048278.6, filed on Jan. 16, 2007, the contents of the foregoing applications are hereby incorporated by reference in their entirety.

FIELD OF THE INVENTION

The present invention falls within the field of pharmaceutical technology. Particularly, it relates to the use of ursolic acid saponin and oleanolic acid saponin in the preparation of medicaments for increasing leucocytes and/or platelets.

BACKGROUND OF THE INVENTION

Due to the phagocytosis of leucocytes, they can eliminate foreign pathogens and safeguard the health of the human body. So, they are called the body defender. There are 4,000-10,000 leucocytes per $mm^3$ in the system of blood circulation of a normal human body. The most important leucocytes are neutrophilic granulocytes having a defensive function, accounting for 50-70% of the total count. Generally, the most frequent and most common leukopenia is neutropenia. When the total leucocyte count is less than 4,000/$mm^3$, body resistance is so low that bacterial infection is easily caused and life is threatened in severe cases. Platelets are one of the blood visible components. The number of platelets in human blood varies greatly, with a normal value of 150,000-300,000/microlitre. Platelets have the functions of stopping bleeding and engulfing viruses, bacteria and other particles, and can nourish and support the capillary endothelial cells to decrease capillary fragility. If the number of platelets significantly decreases or some function disorder occurs, it will lead to a bleeding tendency. Leukopenia and/or thrombocytopenia is common in clinical, including a primary type, a concurrent type and a secondary type. In addition to geneogenous leukopenia and/or thrombocytopenia, there are a variety of causes. Diseases, drugs, radiations, infections, toxins, chemicals, surgical treatments, environmental factors and the like are all likely to cause leukopenia and/or thrombocytopenia. The diseases causing leukopenia and/or thrombocytopenia include hematopoietic system diseases, immune system diseases, infections, systemic lupus erythematosus, allergic shock and thrombocytopenic purpura, etc. Both myeloproliferative disorder and aplastic anemia may be accompanied with leukopenia and/or thrombocytopenia. Bone marrow transplant and liver transplant also directly result in the decrease of leucocytes and/or platelets. Especially for cancer patients, radiotherapy and chemotherapy often cause inhibition of bone marrow hematopoiesis, of which the manifestation is an obvious decrease of peripheral leucocytes and platelets. At present, drugs for treating various types of leukopenia and/or thrombocytopenia are not many yet. The effect of products of genetic engineering, such as granulocyte colony-stimulating factor (GCSF) and granulocyte-macrophage colony-stimulating factor (GMCSF), in increasing leucocyte is remarkable. The Chinese traditional medicine, Sanguisorba Tablet is widely used to increase the number of Leucocytes too, while there are few chemical medicines with significant therapeutic efficacy. Thus, there is a wide need of chemical medicines which can be effective in treating leukopenia and/or thrombocytopenia, convenient to use, easy to control the quality, and easy to obtain by synthesis.

Pentacyclic triterpenes, one type of the naturally distributed triterpenes compounds, are found to have a wide physiological activity. Ursolic acid and oleanolic acid, the most representative compounds thereof, are widely present in the plant kingdom and can be obtained in a large amount. Oleanolic acid has been used for the treatment of liver diseases for many years. In addition to the beneficial effect on liver, both have a variety of other activities according to reports. In the article entitled "Effects of oleanolic acid and ursolic acid on inhibiting tumor growth and enhancing the recovery of hematopoietic system postirradiation in mice (Cancer letter 7-13, 111, 1997)", Lin et al. studied the effect of ursolic acid and oleanolic acid in inhibiting tumor cell growth and found that ursolic acid and oleanolic acid were effective in increasing leucocytes when they were administrated through abdominal cavity in the doses of 25, 50 and 100 mg/kg, and the effect was obvious in the case of a high dose, wherein ursolic acid was more effective than oleanolic acid. Japanese patent No. JP7048260 also discloses the effect of ursolic acid in increasing erythrocytes and platelets. Chinese patent No. CN03135776 discloses the remarkable effect of triterpenoid saponins in increasing leucocytes and platelets, wherein the triterpenoid saponins are isolated from sanguisorba and mainly have 19-hydroxy ursolic acid (also known as pomolic acid) as an aglycon. Since sanguisorba comprises a series of saponins of such type with similar structures and polarities and with a limited content, it is difficult to separate out and purify the effective monomers in batches for medical use; in addition, the pomolic acid or the aglycon thereof per se is not widely present in natural products, thus it is not easy to obtain them in a large amount in the sight of isolation and extraction; and in the sight of synthesis, it is not easy to obtain 19-hydroxy via simple conversion procedures original from ursolic acid, as a raw material, which is easy to obtain, thus there are certain limitations of its exploitation and utilization.

So far, the use of ursolic acid saponins and oleanolic acid saponins in the preparation of medicaments for increasing leucocytes and/or platelets has not been reported. In the present invention, ursolic acid and oleanolic acid, which are widely distributed in natural products, cheap and easy to get, being creatively used as raw materials, and with the introduction of hydrophilic groups, i.e. monosaccharyls or oligosaccharyls by structural modification, it has been proved that saponins can not only improve the water solubility of the parent nucleus, but also have an activity of remarkably increasing leucocytes and/or platelets by pharmacological tests. Compared to pomolic acid saponin isolated from sanguisorba, the patented compounds not only show up stronger pharmacological activities, but also have advantages of synthesis of simple steps, adaptation to industrial production, low cost and so on.

SUMMARY OF THE INVENTION

The technical solution of the present invention provides the use of ursolic acid saponins and oleanolic acid saponins of formula (I) or their pharmaceutically acceptable salts and esters in preparing pharmaceuticals for increasing leucocytes and/or platelets. Formula (I) is:

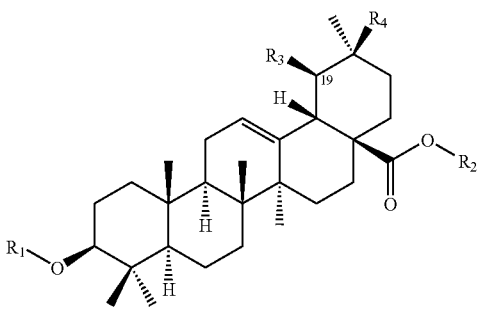

wherein R1 is hydrogen, glucosyl, arabinosyl, rhamnosyl, galactosyl, xylosyl, ribosyl, lyxosyl, mannosyl, allosyl, altrosyl, gulosyl, fructosyl, sorbosyl, quinovosyl, fucosyl, piscosyl, 2-aminoglucosyl, galacturonyl, glucuronyl, or oligosaccharyl formed of 2-5 of such monosaccharide;

R2 is hydrogen, glucosyl, arabinosyl, rhamnosyl, galactosyl, xylosyl, ribosyl, lyxosyl, mannosyl, allosyl, altrosyl, gulosyl, fructosyl, sorbosyl, quinovosyl, fucosyl, piscosyl, 2-aminoglucosyl, galacturonyl, glucuronyl, or oligosaccharyl formed of 2-5 of such monosaccharides; and R1 and R2 are not hydrogen at the same time.

The compound is ursolic acid saponin when R3 is $CH_3$ and R4 is H, represented by formula (II):

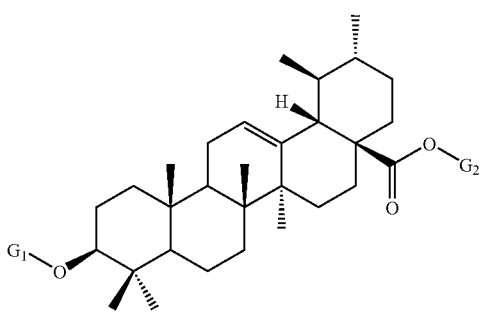

Further, when G1 and G2 of formula (II) are the same monosaccharyl or oligosaccharyl, it is called bisglycosyl ursolic acid saponin. When G1 and G2 are hydrogen, monosaccharyl or oligosaccharyl and G1 is different from G2, it is called non-bisglycosyl ursolic acid saponin.

Wherein, said glycosyl is glucosyl, arabinosyl, rhamnosyl, galactosyl, xylosyl, glucuronyl, or oligosaccharyl formed of 2-5 of such monosaccharides.

Further, bisglycosyl ursolic acid saponin of formula (II) is selected from the group consisting of:
3-O-(α-L-arabopyranosyl) ursolic acid-28-O-(α-L-arabopyranosyl) ester,
3-O-(α-L-rhamnopyranosyl) ursolic acid-28-O-(α-L-rhamnopyranosyl) ester, and
3-O-(β-D-glucopyranosyl) ursolic acid-28-O-(β-D-glucopyranosyl) ester.

Further, non-bisglycosyl ursolic acid saponin of formula (II) is selected from the group consisting of:
3-O-(β-D-galactopyranosyl) ursolic acid,
3-O-(α-L-rhamnopyranosyl) ursolic acid,
3-O-(α-L-arabopyranosyl) ursolic acid,
3-O-(β-D-glucopyranosyl) ursolic acid,
3-O-(α-L-arabopyranosyl) ursolic acid-28-O-(β-D-glucopyranosyl) ester,
3-O-(α-L-arabopyranosyl) ursolic acid-28-O-(β-cellobiosyl) ester, and
ursolic acid-28-O-(α-L-arabopyranosyl) ester.

Still further, bisglycosyl ursolic acid saponin of formula (II) is preferably selected from the group consisting of:
3-O-(α-L-arabopyranosyl) ursolic acid-28-O-(α-L-arabopyranosyl) ester,
3-O-(α-L-arabopyranosyl) ursolic acid and its sodium salts,
3-O-(α-L-arabopyranosyl) ursolic acid-28-O-(β-D-glucopyranosyl) ester, and
3-O-(β-D-glucopyranosyl) ursolic acid-28-O-(β-D-glucopyranosyl) ester.

Still further, the compound of formula (II) is more preferably selected from:
3-O-(α-L-arabopyranosyl) ursolic acid-28-O-(α-L-arabopyranosyl) ester.

The present invention also provides the use of ursolic acid saponins of the above formula (II) in preparing a pharmaceutical for increasing leucocytes and platelets.

According to the use of ursolic acid saponin and oleanolic acid of formula (I), when R3 is H and R4 is $CH_3$, the compound is oleanolic acid saponin, represented by formula (III):

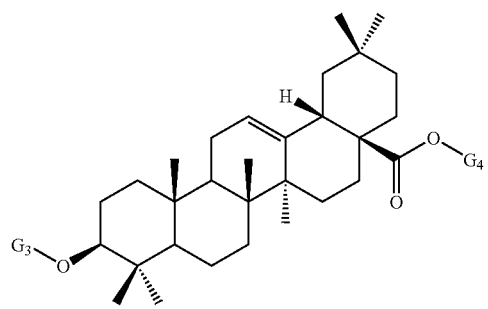

Wherein, G3 and G4 are hydrogen, glucosyl, arabinosyl, rhamnosyl, galactosyl, xylosyl, glucuronyl, or oligosaccharyl formed of 2-5 of such monosaccharides, and G3 and G4 are not hydrogen at the same time.

Further, the compound of general formula (III) is selected from the group consisting of:
3-O-(β-D-glucuronopyranosyl) oleanolic acid,
3-O-(β-D-xylopyranosyl) oleanolic acid,
3-O-(α-L-galactopyranosyl) oleanolic acid,
3-O-(α-L-arabopyranosyl) oleanolic acid and its sodium salts,
3-O-(β-D-glucopyranosyl) oleanolic acid and its sodium salts,
3-O-(α-L-arabopyranosyl) oleanolic acid-28-O-(α-L-arabopyranosyl) ester,
3-O-(β-D-glucopyranosyl) oleanolic acid-28-O-(β-D-glucopyranosyl) ester,
oleanolic acid-28-O-(β-gentiobiosyl) ester,
oleanolic acid-28-O-(β-D-glucopyranosyl) ester.

Still further, the compound of formula (III) is selected from the group consisting of:
3-O-(α-L-arabopyranosyl) oleanolic acid-28-O-(α-L-arabopyranosyl) ester, and
3-O-(β-D-glucopyranosyl) oleanolic acid-28-O-(β-D-glucopyranosyl) ester.

The present invention also provides the use of oleanolic acid saponins of the above formula (III) in preparing pharmaceuticals for increasing platelets.

Wherein, said pharmaceuticals for increasing leucocytes and/or platelets are used to prevent and treat primary, concurrent and secondary leukopenia and/or thrombocytopenia in mammals.

The said pharmaceuticals for increasing leucocytes and/or platelets can also be used separately or in combination to prevent and treat infectious diseases.

Wherein, said leukopenia and/or thrombocytopenia may be caused by diseases, drugs, radiations, infections, toxins, chemical substances, surgical treatments and environmental factors.

Wherein, diseases that cause leukopenia and/or thrombocytopenia include hematopoietic system diseases, immune system diseases, infective diseases, systemic lupus erythematosus(SLE), anaphylactic shock, thrombocytopenic purpura and chemicotherapy for cancer patients.

The present invention provides a pharmaceutical composition useful for increasing human leucocytes and/or platelets, which is a pharmaceutical preparation prepared from any one of the compounds of formulae (I), (II) and (III) or their pharmaceutically acceptable salts, hydrates or solvates of the salts, esters or prodrugs, as an active ingredient, in combination with pharmaceutically acceptable excipients or carriers.

Further, said pharmaceutical preparations may be in the form of tablets, capsules, pills, injections, sustained-release preparations, controlled-release preparations, or various microparticulate drug delivery systems.

According to the general rules of body metabolism and the common knowledge comprehensible to those skilled in the art of pharmacochemistry, the compounds of formulae I-III can be derived by ester linkage, and those compounds of formulae I-III with acidic or alkaline radicals can also be prepared into pharmaceutically acceptable salts. The use of such pharmaceutically acceptable salts, hydrates or solvates of the salts, or esters, particularly predrugs which can be metabolized in vivo into the compounds of formulae I-III, in preparing pharmaceuticals for increasing leucocytes and/or platelets is also covered by this invention. Also, the use of the traditional Chinese medicine, herbal medicine and their effective parts containing any one of the compounds of formulae I-III in preparing pharmaceutical for increasing leucocytes and/or platelets is covered by this invention. Still further, this invention also covers the use of a pharmaceutical composition in preparing medicaments for increasing leucocytes and/or platelets, the pharmaceutical composition comprising any one of the compounds of formulae I-III and their pharmaceutically acceptable salts, hydrates or solvates of the salts, esters and prodrugs, the traditional Chinese medicine, herbal medicine and their effective parts containing any one of the compounds of formulae I-III, and pharmaceutically acceptable carriers. The pharmaceutical composition may be in the form of tablets, capsules, pills, injections, sustained-release preparations, controlled-release preparations, or various microparticulate drug delivery systems, and its use in preparing pharmaceuticals for increasing leucocytes and/or platelets is covered by this invention, too.

DETAILED DESCRIPTION OF THE INVENTION

The following examples are used to illustrate this invention in detail but should not be construed as limiting the scope of the invention. The synthetic raw materials used in the invention, such as ursolic acid and oleanolic acid, are commercially available.

Example 1

Preparation of 3-O-(α-L-arabopyranosyl) ursolic acid-28-O-(α-L-arabopyranosyl) ester 1 g (2.2 mmol) of ursolic acid was mixed with 3.4 g (5.7 mmol, 2.6 eq) of 2,3,4-tri-O-benzoyl-β-L-arabopyranosyl-trichloroacetimidate (See J. Org. Chem. 1999, 64, 7265-7266 for the synthesis method of the compound) as an arabinose glycosyl donor and 1.5 g of powdered 4 Å molecular sieve in 20 ml of a dry $CH_2Cl_2$ solution under $N_2$ atmosphere, then 0.03 ml (0.15 eq) of trimethylsilyl trifluoromethanesulfonate (TMSOTf) was added dropwise at −10° C. The reaction mixture was raised to room temperature gradually and stirred overnight, then a small amount of $Et_3N$ (0.3 ml) was added to quench the reaction. After filtration and concentration of the filtrate, the mixture was subjected to silica gel column chromatography and eluted with petroleum ether/ethyl acetate (4/1-2/1) system, and 1.47 g (1.1 mmol) of bisglycosyl intermediate was obtained. The intermediate was dissolved in 30 ml of methanol/dichloromethane (2/1) and 378 mg of NaOMe (7 mmol, 6.4 eq) was added to react for 4 h at room temperature. The reaction mixture was neutralized with acid resin DowexH$^+$, filtered and concentrated, and subjected to silica gel column chromatography (chloroform/methanol, 10/1-6/1). Finally, 0.61 g of white powder was obtained with a total yield of 39%.

$[α]_D^{20}$=+29.0 (C0.72, MeOH)

IR(KBr)cm$^{-1}$: 3330, 2958, 1724, 1068, 926, 852

$^1$HNMR (600 MHz, CD$_3$OD): δppm 5.40 (d, J=5.8 Hz, 1H, H-1"), 5.28 (t, 1H, H-12), 4.30 (d, J=6.8 Hz, 1H, H-1'), 3.81-3.90 (m, 4H), 3.67-3.71 (m, 2H), 3.51-3.60 (m, 4H), 3.15 (dd, J=11.8, 4.4 Hz, 1H, H-3), 2.29 (d, J=11.6 Hz, 1H, H-18), 1.13, 1.06, 0.98, 0.86, 0.84 (s each, 3H each, Me×5), 0.97 (3H, d, J=4.0 Hz), 0.91 (3H, d, J=6.4 Hz), 0.79 (d, J=11.6 Hz, 1H, H-5)

$^{13}$CNMR (150 MHz, CD$_3$OD): δppm 176.5 (C-28), 137.9 (C-13), 125.9 (C-12), 105.7 (C-1'), 94.4 (C-1"), 89.3 (C-3), 72.9, 72.2, 71.4, 69.9, 68.1, 67.0, 64.9 (d), 55.6, 52.7, 48.2, 48.0, 41.9, 39.6, 39.0, 38.8 (d), 38.6, 36.5, 36.2, 32.9, 30.3, 27.9, 27.2, 25.7, 23.7, 23.0, 22.6, 20.1, 17.9, 16.5, 16.2, 15.6, 14.7

ESI-MS (m/z): 743.3 [M+Na]$^+$

Example 2

Preparation of 3-O-(α-L-rhamnopyranosyl) ursolic acid-28-O-(α-L-rhamnopyranosyl) ester Similar to the method in Example 1,2,3,4-tri-benzoyl-β-L-rhamnopyranosyl-trichloroacetimidate was used as a glycosyl donor, and 3-O-(α-L-rhamnopyranosyl) ursolic acid-28-O-(α-L-rhamnopyranosyl) ester was obtained.

$[α]_D^{20}$=−11.8 (C0.17, DMF)

$^1$HNMR (600 MHz, d$_5$-pyridine): δppm 6.75 (1H, s), 5.46 (1H, m), 5.32 (1H, s), 4.56-4.57 (2H, m), 4.52 (1H, dd, J=9.12, 3.2 Hz), 4.47 (1H, dd, J=8.9, 3.2 Hz), 4.38 (1H, t, J=9.3 Hz), 4.29-4.34 (3H, m), 3.17 (H, dd, J=11.8, 4.44 Hz), 2.44 (1H, d, J=11.3 Hz), 1.81 (1H, m), 1.70 (3H, d, J=6 Hz), 1.67 (3H, d, J=6 Hz), 1.17 (3H, s), 1.08 (1H, m), 0.93 (3H, s), 0.92 (6H, s), 0.90 (3H, d, J=6.4 Hz), 0.88 (3H, d, J=6.4 Hz), 0.87 (3H, s), 0.70 (1H, d, J=11.7 Hz)

$^{13}$CNMR (150 MHz, CD$_3$OD): δppm 175.6 (C-28), 138.1 (C-13), 126.1 (C-12), 103.0 (C-1'), 93.6 (C-1"), 89.0 (C-3), 72.7, 72.0, 71.2, 71.1 (d), 71.0, 70.0, 68.5, 55.3, 53.1, 48.5, 48.2, 41.9, 40.0, 39.5, 39.0, 38.6, 38.4, 36.7, 36.5, 33.0, 30.2, 27.6, 27.4, 25.2, 23.8, 23.0, 22.7, 20.0, 18.0, 16.8, 16.4, 16.1, 15.6, 14.6

ESI-MS (m/z): 771 [M+Na]$^{30}$

Example 3

Preparation of 3-O-(β-D-glucopyranosyl) ursolic acid-28-O-(β-D-glucopyranosyl) ester Similar to the method in Example 1, 2,3,4,6-tetra-O-benzoyl-α-D-glucosyl-trichloroacetimidate was used as a glycosyl donor, and 3-O-(β-D-glucopyranosyl) ursolic acid-28-O-(β-D-glucopyranosyl) ester was obtained. $[\alpha]_D^{20}$=+21.7 (C1.02, MeOH) IR(KBr)cm$^{-1}$: 3417, 2925, 1727, 1672, 1456, 1377, 1226, 1075, 1027, 896, 831

$^1$HNMR (600 MHz, CD$_3$OD): δppm 5.33 (d, J=8.3 Hz, 1H, H-1"), 5.24 (t, 1H, H-12), 4.31 (d, J=7.8 Hz, 1H, H-1'), 3.77-3.84 (m, 2H), 3.65-3.68 (m, 2H), 3.28-3.39 (m, 7H), 3.16-3.18 (m, 2H), 2.22 (d, J=11.2 Hz, 1H, H-18), 1.12, 1.05, 0.96, 0.84, 0.83 (s each, 3H each, Me×5), 0.88 (d, J=6.4 Hz, 3H), 0.78 (d, J=11.6 Hz, 1H, H-5)

$^{13}$CNMR (150 MHz, CD$_3$OD): δppm 176.5 (C-28), 137.7 (C-13), 125.9 (C-12), 105.3 (C-1'), 94.3 (C-1"), 89.4 (C-3), 77.2, 76.9 (d), 76.3, 74.3, 72.5, 70.3, 69.8, 61.4, 61.1, 55.7, 52.8, 48.7, 48.0, 41.9, 39.6, 39.0, 38.9, 38.8, 38.6, 36.4, 36.1, 32.9, 30.3, 27.9, 27.2, 25.7, 23.9, 23.0, 22.6, 20.1, 17.9, 16.5, 16.2, 15.7, 14.8

ESI-MS (m/z): 803 [M+Na]$^+$

Example 4

Preparation of ursolic acid-28-O-(α-L-arabopyranosyl) ester

Ursolic acid (195 mg, 0.43 mmol) and 2,3,4-tri-O—benzoyl-L-arabopyranosyl-bromide (316 mg, 1.4 eq) were mixed in a CH$_2$Cl$_2$/H$_2$O (1/1, 10 ml) system, K$_2$CO$_3$ (151 mg, 2.5 eq) and Bu$_4$NBr (56 mg, 0.4 eq) were added, then the mixture was heated under reflux until the reaction was completed. Then 20 ml of CH$_2$Cl$_2$ was added to separate out the aqueous phase, and the organic phase was washed with water and brine, dried and spin dried. The residue was directly used for the next reaction. The above intermediate was dissolved in a CH$_2$Cl$_2$/MeOH (5 ml, 1/1) system and reacted with sodium methoxide (130 mg, 2.5 mmol) at room temperature overnight. After being quenched by adding water, the reaction mixture was extracted with ethyl acetate for several times. The organic phase was combined, washed with water, dried and spin dried. Then the residue was subjected to silica gel column chromatography and eluted with the CHCl$_3$/MeOH system to obtain 200 mg of white powder with a yield of 79%.

$[\alpha]_D^{20}$=+43.0 (C0.97, MeOH)

$^1$HNMR (600 MHz, CD$_3$OD): δppm 5.38 (1H, d, J=5.8 Hz), 5.26 (1H, t, J=3.6 Hz), 3.85-3.88 (2H, m), 3.64-3.69 (2H, m), 3.54-3.56 (1H, m), 3.14 (1H, dd, J=11.6, 4.5 Hz), 2.26 (1H, d, J=11.0 Hz), 1.11 (3H, s), 0.97 (3H, s), 0.96 (3H, d, J=5.9 Hz), 0.95 (3H, s), 0.88 (3H, d, J=6.5 Hz), 0.82 (3H, s), 0.77 (3H, s), 0.74 (1H, d, J=11.8 Hz)

$^{13}$CNMR (150 MHz, CD$_3$OD): δppm 176.5, 137.9, 125.8, 94.4, 78.3, 72.2, 69.9, 67.0, 64.9, 55.4, 52.7, 48.4, 41.9, 39.6, 39.0, 38.8, 38.7, 38.4, 36.7, 36.2, 33.0, 30.3, 29.2, 27.9, 27.4, 26.5, 23.7, 23.0, 22.6, 20.1, 18.1, 16.5, 16.2, 15.0, 14.7

ESI-MS (m/z): 611.0 [M+Na]$^+$

Example 5

Preparation of 3-O-(α-L-arabopyranosyl) ursolic acid and its sodium salt

Ursolic acid (1 g, 2.2 mmol), K$_2$CO$_3$ (0.6 g) and benzyl chloride (0.3 ml) were mixed in DMF (10 ml), and heated to 100° C. until the raw materials reacted completely. After cooling, the reaction mixture was filtered and the filter cake was washed with DMF. The organic phase was combined, poured into 100 ml of water, and filtrated to obtain a white crude product, which was subjected to silica gel column chromatography and eluted with a petroleum ether/ethyl acetate system to obtain 1.09 g of benzyl ursolic acid (2.0 mmol). The above dried intermediate, 1.7 g (2.8 mmol, 1.4 eq) of 2,3,4-tri-O-benzoyl-β-L-arabopyranosyl-trichloroacetimidate as a glycosyl donor, and 1 g of a powdered molecular sieve were mixed in 15 ml of a dried CH$_2$Cl$_2$ under N$_2$ atmosphere, then 78 μl (0.43 mmol) of trimethylsilyl trifluoromethanesulfonate (TMSOTf) was added dropwise at –10° C. The raw material of benzyl ester was tracked by TLC. The reaction was quenched with Et$_3$N after it was complete. After the mixture was filtered, the filtrate was concentrated, subjected to silica gel column chromatography and eluted with petroleum ether/ethyl acetate system to obtain 1.65 g (1.67 mmol) of a glycosyl intermediate, 3-O-(2,3,4-tri-O-benzoyl-α-L-arabopyranosyl)-benzyl ursolic acid. The intermediate was dissolved in 15 ml of a methanol/CH$_2$Cl$_2$ (½), and subjected to hydrogenation at normal pressure overnight under catalysis of 0.1 g of 5% Pd/C. The mixture was filtered, then the filtrate was concentrated, subjected to silica gel column chromatography and eluted with the petroleum ether/ethyl acetate system to obtain 1.26 g (1.4 mmol) of 3-O-(2,3,4-tri-O-benzoyl-α-L-arabopyranosyl) ursolic acid. This product was dissolved in 25 ml of MeOH/CH$_2$Cl$_2$ (2/1) and added with 35 mg (0.65 mmol) of NaOMe to react at room temperature overnight. Then the reaction solution was neutralized with a dilute acetic acid solution, concentrated, subjected to silica gel column chromatography and eluted with a chloroform/methanol system to obtain 0.737 g (1.25 mmol) of 3-O-(α-L-arabopyranosyl) ursolic acid with a total yield of the four-step reaction of 57%.

$[\alpha]_D^{20}$=+41.9 (C0.43, DMF)

$^1$HNMR (600 MHz, CD$_3$OD): δppm 5.22 (1H, t, J=3.6 Hz, H-12), 4.27 (1H, d, J=6.7 Hz, H-1'), 3.82 (1H, dd, J=12.2, 3.4 Hz), 3.79-3.80 (m, 1H), 3.49-3.58 (3H, m), 3.14 (1H, dd, J=11.4, 4.14 Hz, H-3), 2.19 (1H, d, J=11.0 Hz, H-18), 1.11 (3H, s), 1.04 (3H, s), 0.96 (3H, s), 0.84 (3H, s), 0.84 (3H, s), 0.87 (3H, d, J=6.5 Hz), 0.78 (1H, d, J=11.2 Hz, H-5)

$^{13}$CNMR (150 MHz, CD$_3$OD): δppm 175.0, 139.6, 126.9, 107.1, 90.7, 74.3, 72.8, 69.5, 66.4, 57.0, 54.4, 48.0, 42.2, 40.8, 40.4, 40.2, 39.9, 38.1, 37.8, 34.3, 31.8, 29.2, 28.6, 27.0, 25.3, 24.4, 24.1, 21.6, 19.3, 17.8, 17.7, 17.0, 16.1

ESI-MS (m/z): 611.0 [M+Na]$^{30}$ 30 mg of 3-O-(α-L-arabopyranosyl) ursolic acid was dissolved in methanol/chloroform (4 ml, 3/1), added with 5 mg of NaOMe, then stirred at room tempreature for 30 min and filtered to separate out a white solid. The solid was washed with methanol and dried to obtain 3-O-(α-L-arabopyranosyl) ursolic acid sodium salt.

Example 6

Preparation of 3-O-(β-D-glucopyranosyl) ursolic acid and its sodium salt

3-O-(β-D-glucopyranosyl) ursolic acid was obtained through a four-step reaction with ursolic acid as a starting material and 2,3,4,6-tetra-O-benzoyl-α-D-glucopyranosyl-trichloroacetimidate as a glycosyl donor.

$[\alpha]_D^{20}$=+27.0 (C0.2, DMF)

$^1$HNMR (600 MHz, CD$_3$OD): δppm 5.22 (t, 1H, H-12), 4.32 (d, J=7.8 Hz, 1H, H-1'), 3.83 (dd, J=11.8, 2.2 Hz, 1H, H-6'-1), 3.67 (dd, J=12, 5.2 Hz, 1H, H-6'-2), 3.17-3.35 (m, 5H), 2.20 (d, J=11.4, 1H, H-18), 1.11 (3H, s), 1.06 (3H, s), 0.97 (6H, s Me×2), 0.90 (3H, d, J=5.8 Hz), 0.85 (6H, s), 0.78 (d, J=12.4 Hz, 1H, H-5)

$^{13}$CNMR (150 MHz, CD$_3$OD): δppm 178.9 (C-28), 137.0 (C-13), 126.2 (C-12), 103.8 (C-1'), 88.0 (C-3), 75.4, 74.8, 72.8, 68.8, 59.9, 54.2, 51.5, 46.7, 45.0, 40.4, 37.9, 37.5, 37.2, 37.0, 35.2, 34.9, 31.4, 28.9, 27.8, 26.3, 25.7, 24.2, 22.5, 21.5, 21.2, 18.7, 16.4, 14.9, 14.8, 14.1, 13.1

ESI-MS (m/z): 641.5 [M+Na]$^+$

The method for preparing its sodium salt was similar to that in Example 5.

Example 7

Preparation of 3-O-(α-L-arabopyranosyl) ursolic acid-28-O-(β-D-glucopyranosyl) ester Similar to the method in Example 4, the intermediate product, ursolic acid-28-O-(β-D-glucopyranosyl) ester, was obtained from ursolic acid as a starting material. By using 2,3,4-tri-O-benzoyl-β-L-arabopyranosyl-trichloroacetimidate as a secondary glycosyl donor under a similar condition of glycosylation and using NaOMe for deprotection, 3-O-(α-L-arabopyranosyl) ursolic acid-28-O-(β-D-glucopyranosyl) ester was obtained.

$^1$HNMR (600 MHz, CD$_3$OD): δppm 5.36 (d, J=8.2 Hz, 1H, H-1''), 5.26 (t, 1H, H-12), 4.29 (d, J=6.7 Hz, 1H, H-1'), 3.80-3.86 (m, 3H), 3.69 (dd, J=12, 4.6 Hz, 1H, H-6'-1), 3.57-3.58 (m, 1H, H-6'-2), 3.32-3.43 (m, 4H), 3.15 (dd, J=11.6, 2.4 Hz, 1H), 2.24 (d, J=11.2 Hz, 1H, H-18), 1.13 (3H, s), 1.06 (3H, s), 0.99 (6H, s), 0.91 (d, J=6.3 Hz, 3H), 0.86 (3H, s), 0.85 (3H, s), 0.79 (d, J=11.7 Hz, 1H, H-5)

$^{13}$CNMR (150 MHz, CD$_3$OD): δppm 176.5 (C-28), 137.7 (C-13), 125.9 (C-12), 105.7 (C-1'), 94.3 (C-1''), 89.3 (C-3), 77.2, 76.9, 72.9, 72.5, 71.4, 69.8, 68.1, 64.9, 61.1, 55.6, 52.8, 48.2, 41.9, 39.6, 39.0, 38.9, 38.8, 38.6, 36.5, 36.1, 32.9, 30.3, 29.3, 27.9, 27.2, 25.7, 23.9, 23.0, 22.6, 20.1, 17.9, 16.5, 16.2, 15.6, 14.7

ESI-MS (m/z): 773.4 [M+Na]+$_o$

The compound in this example is the closest to 3-O-(α-L-arabopyranosyl)-19-hydroxy-ursolic acid-28-O-(β-D-glucopyranosyl) ester with the highest activity isolated from sanguisorba, and only lacks a 19-hydroxy. The compound of this example can be conveniently synthesized using ursolic acid as a starting material by the method described above, which is easy to put into industrial practice. However, the synthesis of said compound from sanguisorba is a problem, since the raw material, 19-hydroxy-ursolic acid, is not easy to get and, moreover, it is difficult to synthesize it starting from ursolic acid. In addition, there are certain limitations in separating the compound in large quantities directly from natural products. Thus, its use in the medicinal field is, in a way, restricted. One of the creative aspects of the present invention lies in providing a series of compounds which are easier to obtain, can be synthesized starting from the cheap and accessible ursolic acid and oleanolic acid, and have an enhanced activity, thus they can be applied widely to the medicinal field.

Example 8

Preparation of 3-O-(α-L-arabopyranosyl) ursolic acid-28-O-(β-cellobiosyl) ester

It was obtained by a sililar method.

$[\alpha]_D^{20}$=+30.8 (C0.9, MeOH)

$^1$HNMR (600 MHz, CD3OD): δppm 5.36 (1H, d, J=8.3 Hz), 5.24 (1H, t), 4.43 (1H, d, J=7.9 Hz), 4.28 (1H, d, J=6.7 Hz), 3.21-3.89 (16H, m), 3.13 (1H, dd, J=11.4, 4.1 Hz), 2.22 (1H, d, J=11.4 Hz), 1.11 (3H, s), 1.04 (3H, s), 0.96 (6H, s), 0.89 (3H, d, J=6.4 Hz), 0.84 (3H, s), 0.83 (3H, d, J=6.9 Hz), 0.78 (1H, d, J=11.2 Hz)

ESI-MS (m/z): 912 [M]$^+$

Example 9

Preparation of 3-O-(α-L-rhamnopyranosyl) ursolic acid

Similar to the method in Example 5,2,3,4-tri-O-benzoyl-β-L-arabopyranosyl-trichloroacetimidate was used as a glycosyl donor. After glycosylation followed by deprotection, 3-O-(α-L-rhamnopyranosyl) ursolic acid was obtained.

$[\alpha]_D^{20}$=+5.7 (C0.74, MeOH)

$^1$HNMR (600 MHz, d$_5$-pyridine): δppm 5.48 (1H, m), 5.32 (1H, s), 4.55 (1H, t, J=1.6 Hz), 4.46 (1H, dd, J=10.4, 3.4 Hz), 4.26-4.34 (2H, m), 3.17 (1H, dd, J=11.8, 4.4 Hz), 2.62 (1H, d, J=11.4 Hz), 2.31 (1H, dt, J=13.4, 4.4 Hz), 2.12 (1H, dt, J=4.0, 12.6 Hz), 1.87-2.15 (6H, m), 1.66 (3H, d, J=5.8 Hz), 1.56 (1H, m), 1.24 (s, 3H), 1.02 (3H, s), 1.00 (3H, d, J=6.4 Hz), 0.96 (3H, d, J=6.4 Hz), 0.93 (3H, s), 0.83 (3H, s), 0.79 (3H, s), 0.72 (1H, d, J=11.6 Hz)

$^{13}$CNMR (150 MHz, d$_5$-pyridine): δppm 180.2, 138.2, 125.5, 103.0, 89.0, 72.7, 71.2, 71.1, 68.5, 55.3, 53.0, 48.2, 48.0, 47.2, 41.9, 39.4, 39.0, 38.6, 38.4, 36.7, 36.5, 32.9, 30.4, 27.8, 27.4, 25.2, 23.9, 23.0, 22.7, 20.2, 18.0, 16.4 (d), 16.2, 15.6, 14.6

ESI-MS (m/z): 1203 [2M−1]$^+$, 601 [M−1]+

Example 10

Preparation of 3-O-(β-D-galactopyranosyl) ursolic acid

Similar to the method in Example 5,2,3,4,6-tetra-O-benzoyl-α-D-galactopyranosyl-trichloroacetimidate was used as a glycosyl donor. After glycosylation followed by deprotection, 3-O-(β-D-galactopyranosyl) ursolic acid was obtained.

$[\alpha]_D^{20}$=+13.8 (C0.8, MeOH)

$^1$HNMR (600 MHz, d5-pyridine): δppm 5.48 (1H, t, J=3.2 Hz), 4.93 (1H, d, J=6.6 Hz), 4.57 (1H, d, J=3.2 Hz), 4.43-4.48 (3H, m), 4.16 (1H, dd, J=9.6, 3.4 Hz), 4.11 (1H, t, J=6.2 Hz), 3.41 (1H, dd, J=11.8, 4.4 Hz), 2.62 (1H, d, J=11.6 Hz), 2.20-2.32 (2H, m), 2.12 (1H, m), 1.57 (1H, t, J=8.0 Hz), 1.31 (3H, s), 1.26 (3H, s), 1.01 (3H, s), 1.00 (3H, d, J=5.8 Hz), 0.96 (3H, d, J=5.2 Hz), 0.96 (3H, s), 0.85 (3H, s), 0.80 (1H, d, J=11.8 Hz)

ESI-MS (m/z): 641 [M+Na]$^+$

Example 11

Preparation of 3-O-(α-L-arabopyranosyl) oleanolic acid-28-O-(α-L-arabopyranosyl) ester Similar to the method in Example 1,2,3,4-tri-O-benzoyl-β-L-arabopyranosyl-trichloroacetimidate was used as a glycosyl donor. After a glycosylation reaction followed by deprotection using sodium methoxide, the title compound was obtained.

$[\alpha]_D^{20}$=+35.5 (C0.71, MeOH)

$^1$HNMR (600 MHz, CD$_3$OD): δppm 5.41 (1H, d, J=5.7 Hz, H-1"), 5.27 (1H, t, H-12), 4.27 (1H, d, J=6.7 Hz), 3.79-3.90 (4H, m), 3.66-3.70 (2H, m), 3.55-3.58 (2H, m), 3.49-3.52 (2H, m), 3.13 (1H, dd, H-3), 2.00-2.06 (1H, m, H-18), 1.15, 1.04, 0.95, 0.94, 0.90, 0.83, 0.79 (each 3H, s, Me×7)

ESI-MS (m/z): 743.5 [M+Na]$^{30}$

Example 12

Preparation of 3-O-(β-D-glucopyranosyl) oleanolic acid-28-O-(β-D-glucopyranosyl) ester 2,3,4,6-tetra-O-benzoyl-α-D-glucopyranosyl-trichloroacetimidate was used as a glycosyl donor. Similar to Example 1, the title compound was obtained.

$^1$HNMR (600 MHz, CD$_3$OD): δppm 5.37 (d, J=8.1 Hz, 1H, H-1"), 5.25 (m, 1H, H-12), 4.31 (d, J=7.86 Hz, 1H, H-1'), 3.17-3.84 (13H, m), 2.85 (1H, m), 1.16, 1.05, 0.95, 0.93, 0.89, 0.84, 0.80 (s each, 3H each, Me×7)

ESI-MS (m/z): 803 [M+Na]$^+$

Example 13

Preparation of 3-O-(β-D-glucopyranosyl) oleanolic acid

Similar to Example 5.

$^1$H NMR (600 MHz, CD$_3$OD): δppm 5.26 (1H, t, J=3.6 Hz), 4.34 (1H, d, J=7.9 Hz), 3.86 (1H, dd, J=11.8, 2.3 Hz), 3.68 (1H, dd, J=11.8, 5.3 Hz), 3.19-3.37 (5H, m), 2.88 (1H, m), 1.18, 1.08, 0.98, 0.97, 0.92, 0.88, 0.86 (each 3H, s), 0.81 (1H, d, J=11.6 Hz)

$^{13}$C NMR (150 MHz, CD$_3$OD): δppm 181.5 (C-28), 144.1 (C13), 122.0 (C12), 105.3 (C'1), 89.4 (C3), 76.9-70.3 (C'4, C'5, C'3, C'2), 61.4 (C6), 55.7 (C5), 48.2 (C9), 47.2 (C19), 46.5 (C17), 46.1 (C18), 41.5 (C14), 39.2 (C8), 38.8 (C1), 38.4 (C4), 36.5 (C10), 33.7 (C21), 32.7 (C29), 32.6 (C7), 32.2 (C22), 30.4 (C20), 27.5 (C23), 27.2 (C15), 25.6, 25.0 (C27, C25), 23.1 (C-30), 22.8 (C11), 22.7 (C16), 18.0 (C6), 16.4 (C26), 15.6 (C24), 14.5 (C25)

The method for preparing its sodium salt was the same as before.

Example 14

Preparation of 3-O-(β-D-glucopyranosyl) oleanolic acid

Similar to Example 5.

$^1$H NMR (600 MHz, d$_6$-DMSO): δppm 12.00 (brs, 1H), 5.16 (s, 1H, H12), 4.71 (d, J=4.7 Hz, 1H), 4.60 (d, J=5.5 Hz, 1H), 4.50 (t, J=5.8 Hz, 1H), 4.29 (d, J=4.4 Hz, 1H), 4.10 (d, J=7.3 Hz, 1H), 3.6 (t, J=3.7 Hz, 1H, H4), 3.54-3.50 (m, 1H), 3.39-3.42 (m, 1H), 3.23-3.29 (m, 3H), 3.02 (dd, J=4.7, 11.4 Hz, 1H, H3), 2.80 (dd, J=3.3, 13.6 Hz, 1H, H18), 1.89-1.93 (m, 1H), 1.80-1.77 (m, 3H), 1.09 (s, 3H), 0.98 (S, 3H), 0.87 (S, 9H), 0.75 (s, 3H), 0.71 (s, 3H)

$^{13}$CNMR (150 MHz, d6-DMSO): δppm 178.6 (C28), 143.8 (C13), 121.5 (C12), 106.0 (C'1), 87.8 (C3), 74.8-68.0 (C'4, C'5, C'2, C'3), 60.3 (C'6), 54.9 (C5), 47.0 (C9), 45.7 (C19), 45.2 (C17), 41.2 (C18), 40.8 (C14), 38.8 (C8), 38.7 (C1), 38.1 (C4), 36.3 (C10), 33.3 (C21), 32.8 (C29), 32.3 (C7), 32.1 (C22), 30.4 (C20), 27.6 (C23), 27.1 (C15), 25.6 (C27), 25.5 (C25), 23.3 (C30), 22.9 (C11), 22.6 (C16), 17.7 (C6), 16.8 (C26), 16.4 (C24), 15.1 (C25)

Example 15

Preparation of 3-O-(β-D-xylopyranosyl) oleanolic acid 2,3,4-tri-O-benzoyl-α-D-xylopyranosyl-trichloroacetimidate was used as a glycosyl donor. Similar to Example 5, 3-O-(β-D-xylopyranosyl) oleanolic acid was obtained.

$^1$H NMR (600 MHz, d$_6$-DMSO): δppm 12.00 (brs, 1H, COOH), 5.16 (brs, 1H, H12), 4.89-4.91 (m, 3H), 4.11 (d, J=7.8 Hz, 1H, H1), 3.63 (dd, J=5.0, 11.0 Hz, 1H), 3.21-3.26 (m, 1H), 2.92-3.07 (m, 4H), 2.73 (dd, J=3.7, 13.7 Hz, 1H), 1.89-1.93 (m, 1H), 1.79 (brd, J=8.7 Hz, 2H), 1.09 (s, 3H), 0.97 (s, 3H), 0.87 (s, 6H), 0.85 (s, 3H), 0.75 (s, 3H), 0.71 (s, 3H)

$^{13}$CNMR (150 MHz, d$_6$-DMSO): δppm 178.6 (C28), 143.8 (C13), 121.5 (C12), 106.2 (C'1), 87.6 (C3), 76.7 (C'3), 73.7 (C'2), 69.6 (C'4), 65.5 (C'5), 54.9 (C5), 46.9 (C9), 45.7 (C19), 45.4 (C17), 41.3 (C18), 40.8 (C14), 38.8 (C8), 38.7 (C1), 37.9 (C4), 36.3 (C10), 33.3 (C21), 32.8 (C29), 32.3 (C7), 32.1 (C22), 30.3 (C20), 27.4 (C23), 27.2 (C15), 25.7 (C27), 25.5 (C2), 23.4 (C30), 22.9 (C11), 22.6 (C16), 17.7 (C6), 16.8 (C26), 16.4 (C24), 15.0 (C25)

Example 16

Preparation of 3-O-(α-L-arabopyranosyl) oleanolic acid

Similar to Example 5.

$^1$H NMR (600 MHz, d$_6$-DMSO): δppm 12.01 (s, 1H, COOH), 5.15 (t, J=3.6 Hz, 1H, H12), 4.81 (d, J=4.7 Hz, 1H), 4.52 (d, J=5.9 Hz, 1H), 4.47 (d, J=4.4 Hz, 1H), 4.11 (d, J=6.2 Hz, 1H, H1), 3.64 (dd, J=3.3, 12.5 Hz, 1H), 3.58 (brs, 1H), 3.33-3.34 (m, 3H), 3.00 (dd, J=4.4, 11.4 Hz, 1H, H3), 2.74 (dd, J=5.4, 13.6 Hz, 1H), 1.88-1.93 (m, 1H), 1.79 (dd, J=3.3, 8.4 Hz, 2H, H11), 1.09 (s, 3H, H-27), 0.96 (s, 3H, H23), 0.87 (s, 9H), 0.75 (s, 3H), 0.71 (s, 3H)

$^{13}$CNMR (150 MHz, d$_6$-DMSO): δppm 178.6 (C28), 143.8 (C13), 121.5 (C12), 105.8 (C1), 87.6 (C3), 72.7, 70.9, 67.6, 65.1, 54.9, 46.9, 45.7, 45.4, 41.3, 40.8, 38.8, 38.7, 38.0, 36.3, 33.3, 32.8, 32.3, 32.0, 30.4, 27.6, 27.2, 25.7, 25.5, 23.4, 22.9, 22.6, 17.7, 16.8, 16.4, 15.1

The method for preparing its sodium salt was the same as before. The spectral data of the compounds in Examples 13, 14, 15 and 16 are identical to the data in this literature, Journal of Ocean University of China (2005, 35(4): 635-640).

Example 17

Preparation of oleanolic acid-28-O-(β-D-glucopyranosyl) ester 2,3,4,6-tetra-O-benzoyl-α-D-glucopyranosyl-bromide and oleanolic acid were used as raw materials. After phase-transfer glycosylation similar to Example 4 followed by deprotection using sodium methylate, the title compound was obtained.

m.p. 180-183° C., $[\alpha]_D^{20}$=+22 (C0.2, pyridine)

IR(KBr) cm$^{-1}$: 3435, 2933, 2862, 1695, 1461, 1386, 1181, 1030, 996, 762

$^1$HNMR (600 MHz, d$_5$-pyridine): δppm 6.19 (1H, d, J=8 Hz, H'-1), 5.35 (1H, brs, H12), 1.18, 1.17, 1.13, 1.06, 0.91, 0.90, 0.86 (21H, s, 7 Me)

$^{13}$CNMR: δppm 176.9, 144.7, 123.4, 92.3, 79.8, 79.4, 78.6, 74.6, 71.6, 62.7, 56.3, 48.7, 47.5, 46.7, 42.3, 40.4, 40.0, 39.5, 37.9, 34.5, 33.6, 33.0, 31.3, 30.5, 29.3, 28.8, 28.6, 26.6, 24.3, 23.9, 24.3, 24.2, 23.9, 18.0, 17.0, 16.1

ESI-MS (m/z): 641 [M+Na]$^{30}$

Example 18

Preparation of oleanolic acid-28-O-(β-gentiobiosyl) ester

Fully acetylated gentiobiosyl-bromide and oleanolic acid were used as raw matarials. After phase-transfer glycosylation similar to Example 4, followed by deprotection using sodium methylate, the title compound was obtained. m.p. 248-250° C.

$^1$H NMR (600 MHz, CD$_3$OD): δppm 5.41 (1H, d, J=7.8 Hz, H'1), 5.32 (1H, d, H12), 4.41 (1H, d, J=8.7 Hz, H"-1), 4.18 (1H, d, J=11.6 Hz), 3.91 (1H, d, J=13.6 Hz), 3.83 (1H, dd, J=6, 5.5 Hz), 3.73 (1H, dd, J=5.5, 5.5 Hz), 1.22, 1.03, 1.01, 1.00, 0.97, 0.87, 0.84 (21H, s, 7×Me)

Example 19

Preparation of 3-O-(β-D-glucuronopyranosyl) oleanolic acid

Under reaction conditions similar to those in Example 5, the title compound was obtained by glycosylation and the subsequent deprotection.

$^1$HNMR (600 MHz, d$_5$-pyridine): δppm 5.65 (1H, brs, H12), 4.82 (1H, d, J=7 Hz, H'-1), 1.33, 1.32, 1.29, 1.04, 0.99, 0.98, 0.79 (21H, s, 7×Me)

ESI-MS (m/z): 655 [M+Na]$^{30}$

Next, the beneficial effects of the present invention will be confirmed through pharmacodynamic tests.

In vitro experiments of growth rate of bone marrow monocyte proliferation were carried out on the compounds in the examples, and in vivo experiments of increasing leucocytes and/or platelets in mice were carried out on some compounds in the examples. By comparison of the therapeutic effects of 3-O-(α-L-arabopyranosyl)-19-hydroxy-ursolic acid-28-O-(β-D-glucopyranosyl) eater which is a monomer saponin isolated from sanguisorba, ursolic acid and oleanolic acid, the result confirms the beneficial effects of the present invention.

Experimental Example 1

Effect in Promoting Monocytic Proliferation in Bone Marrow of Mice Cultured In Vitro 15-20 KunMing mice (purchased from Laboratory Animal Center of Zhengzhou University, Henan) of either sex were killed by cervical vertebral dislocation. Bilateral thighbones were isolated and caput femoris was cut off. The marrow was washed repeatedly with serum-free RPMI1640 (Gibco Corp.), the wash solution containing marrow cells was collected, sucked and blew repeatedly with a pipette to make the cells disperse. After standing for a moment, the supernatant was sucked up and centrifugated at 100 g for 3 min to collect the cell pellet. The cells were resuspended in a culture media and brought to a volume of 5 ml. The cell suspension was added to the upper layer of a centrifugal tube containing 5 ml of a lymphocyte separation medium of mice and centrifugated at 400 g for 30 min. The milk-white bone marrow mononuclear cell (BMMNC) layer in the middle of the interface was collected and washed with serum-free medium RPMI1640 for three times to obtain a BMMNC suspension, which was inoculated into a 96-well plate at forty thousand per well after counting. Positive drugs rhG-CSF (recombinant granulocyte colony-stimulating factor, manufactured by QI LU Pharmaceutical Co., LTD., Shandong) or test samples of different concentrations were added, and meanwhile a blank control group without drug was established. They were cultured in a 5% CO$_2$ incubator at 37 for 5 days. Cell proliferation was measured by a conventional SRB (Sigma) method in which OD at 490 nm was measured after being dyed with SRB. The growth rates of cell proliferation after drug treatment were calculated (Growth rate of cell proliferation=experimental group-blank control group/blank control group*100%). The experimental results are shown in Table 1.

TABLE 1

Sample number and growth rate of monocytic proliferation in bone marrow of mice (%)

| Sample Number | Compound | Growth Rate of Proliferation %, 1 µg/ml |
|---|---|---|
| Blank | | 0 |
| G-1 | 3-O-(α-L-arabopyranosyl) ursolic acid-28-O-(α-L-arabopyranosyl) ester | 31.3 |
| G-2 | 3-O-(α-L-rhamnopyranosyl) ursolic acid-28-O-(α-L-rhamnopyranosyl) ester | 19.9 |
| G-3 | 3-O-(β-D-glucopyranosyl) ursolic acid-28-O-(β-D-glucopyranosyl) ester | 25.2 |
| G-4 | 3-O-(α-L-arabopyranosyl) ursolic acid-28-O-(β-cellobiosyl) ester | 18.0 |
| G-5 | ursolic acid-28-O-(α-L-arabopyranosyl) ester | 20.1 |
| G-6 | 3-O-(α-L-arabopyranosyl) ursolic acid | 29.9 |
| G-7 | 3-O-(β-D-glucopyranosyl) ursolic acid | 23.7 |
| G-8 | 3-O-(α-L-arabopyranosyl) ursolic acid-28-O-(β-D-glucopyranosyl) ester | 29.5 |
| G-9 | 3-O-(α-L-rhamnopyranosyl) ursolic acid | 23.4 |
| G-10 | 3-O-(β-D-galactopyranosyl) ursolic acid | 24.2 |
| G-11 | 3-O-(α-L-arabopyranosyl) oleanolic acid-28-O-(α-L-arabopyranosyl) ester | 26.8 |
| G-12 | 3-O-(β-D-glucopyranosyl) oleanolic acid-28-O-(β-D-glucopyranosyl) ester | 25.4 |
| G-13 | 3-O-(β-D-glucopyranosyl) oleanolic acid | 21.6 |
| G-14 | 3-O-(β-D-galactopyranosyl) oleanolic acid | 19.9 |
| G-15 | 3-O-(β-D-xylopyranosyl) oleanolic acid | 20.6 |
| G-16 | 3-O-(α-L-arabopyranosyl) oleanolic acid | 21.6 |
| G-17 | oleanolic acid-28-O-(β-D-glucopyranosyl) ester | 20.6 |
| G-18 | oleanolic acid-28-O-(β-gentiobiosyl) ester | 19.0 |
| G-19 | 3-O-(β-D-glucuronopyranosyl) oleanolic acid | 20.9 |
| G-20 | oleanolic acid | 4.5 |
| G-21 | ursolic acid | 7.9 |
| G-22 | 3-O-(α-L-arabopyranosyl)-19-hydroxy-ursolic acid-28-O-(β-D-glucopyranosyl) ester | 15.2 |
| Positive | G-CSF | 33.2 (5 pg/ml) |

Results and Discussion

As shown in Table 1, the growth rates of proliferation of samples G1-G19 according to the present invention are more than 10% higher than those of ursolic acid and oleanolic acid, and the difference is remarkable. G-22 isolated from sanguisorba is a compound with the strongest activity among those disclosed in Chinese Patent No. CN03135776. Sample G-8 has a structure quite similar to that of G-22 and is only different in lacking 19-hydroxy. Results shown in the above table suggest that the saponin with ursolic acid or oleanolic acid as an aglycon according to the present invention have advantages of simple synthesis and enhanced activity, compared with the saponin with pomolic acid as an aglycon.

It also can be seen from the above data that with respect to G-1, G-3, G-6 and G-8 of ursolic acid saponin, G-11 and G-12 of oleanolic acid saponin have higher growth rates of proliferation, so the above-mentioned compounds were preferably selected and studied using an in vivo experimental method.

Further, in vivo experiments were carried out on the compounds involved in the present invention using animal models of cyclophosphamide-induced leukopenia in mice. Experimental methods are briefed as follows: Healthy Kunming mice, of which half were male and the other half were female, were divided into groups, each group incuding 18 mice, and those mice weighing 18-22 g were selected and divided into groups randomly according to their body weights. Each group was given a different drug, wherein the negative control group and model control group were given physiological saline of the same volume, and the positive control group was treated with granulocyte colony-stimulating factors 40 μg/kg through subcutaneous injection (injection volume: 0.1 ml/10 g). After administration for 3 days, except the negative control group, other treatment groups were treated with 100 mg/kg cyclophosphamide (CY) through lumbar injection once a day for three days to cause a decrease of leukocytes in mice. A drop of blood (20 μl) was taken from posterior orbital venous plexus to detect the hemogram to observe the situation of leukocytes and platelets on day 1, day 3 and/or day 5 after the final lumbar injection of cyclophosphamide (i.e day 1, day 3 and/or day 5 after modeling) (Note: Each treatment group was administrated incessantly). The mice were killed on day 5 after the final lumbar injection of cyclophosphamide (i.e day 5 after modeling), and the leukocytes (WBC) and platelets (PLT) of the hemogram index were counted.

Experimental Example 2

Effect of Ursolic Acid Saponin on Leukocytes (WBC) of Animal Model of Cyclophosphamide-Induced Leukopenia in Mice This experiment mainly studies the effect of G-1, G-6 and G-8 of ursolic acid saponin in increasing leukocytes, and compares the therapeutic effects of aglycon of ursolic acid and oleanolic acid and of the compound G-22 which has been disclosed by a patent. The results are shown in Table 2:

TABLE 2

Effect of ursolic acid saponin on leukocytes (WBC) of animal model of CY-induced leukopenia in mice

| Group | Dosage | Day1 after modeling Statistics | Day 3 after modeling Statistics | Day 5 after modeling |
|---|---|---|---|---|
| negative control group | — | 8.89 ± 3.45**★★ | 9.28 ± 3.44**★★ | 9.14 ± 4.9 |
| model control group | — | 0.87 ± 0.27 | 3.74 ± 1.92 | 8.17 ± 3.6 |
| G-1 | 0.8 mg/kg | 1.14 ± 0.56Δ | 7.85 ± 3.00**★★ | 15.46 ± 10.44* |
| G-6 | 0.8 mg/kg | 1.19 ± 0.47* | 7.13 ± 2.61**★ | 17.16 ± 14.13* |
| G-8 | 0.8 mg/kg | 0.85 ± 0.39 | 6.91 ± 2.54**★ | 15.32 ± 9.07** |
| G-20 | 0.8 mg/kg | 0.99 ± 0.40 | 3.88 ± 2.01 | 7.00 ± 3.22 |
| G-21 | 0.8 mg/kg | 1.01 ± 0.47 | 3.94 ± 1.73 | 7.07 ± 3.14 |
| G-22 | 0.8 mg/kg | 1.08 ± 0.34Δ | 5.17 ± 1.77* | 11.87 ± 9.53 |
| G-CSF | 40 μg/kg | 1.17 ± 0.33* | 5.93 ± 3.10* | 13.18 ± 5.53** |

Note:
Compared with the model control group between groups,
*P < 0.05,
**P < 0.01,
Δstands for a good trend.
Compared with G-22 between groups,
★P < 0.05,
★★P < 0.01.

It can be seen from the above table that there is an obvious difference in increasing leukocytes under the dose of 0.8 mg/kg between G-1, G-6 and G-8 of ursolic acid saponin provided in the present invention and the disclosed G-22, especially on day 3 after modeling. However, G-20 and G-21 of aglycon have no obvious effect in increasing leukocytes.

Experimental Example 3

Effect of Ursolic Acid Saponin and Oleanolic Acid Saponin on Leukocytes (WBC) and Platelets of Animal Model of Cyclophosphamide-Induced Leukopenia in Mice The purpose of this experiment is to study the effect of G-1, G-3, G-11 and G-12 of ursolic acid saponin and oleanolic acid saponin in increasing platelets, and to observe whether G-11 and G-12 of oleanolic acid saponin have an effect in increasing leukocytes. The experimental method is the same as above, and the results are shown in the following table.

TABLE 3

Effect of ursolic acid saponin and oleanolic acid saponin on leukocytes of animal model of CY-induced leukopenia in mice

| Group | Dosage (/kg) | Day 1 after modeling Statistics | Day 5 after modeling Statistics |
|---|---|---|---|
| negative control group | — | 6.68 ± 2.27**★★ | 6.52 ± 2.24 |
| model control group | — | 0.50 ± 0.19 | 5.42 ± 1.99 |
| G-1 | 0.8 mg/kg | 0.98 ± 0.55** | 9.33 ± 5.17** |
| G-3 | 0.8 mg/kg | 1.16 ± 0.53** | 5.62 ± 2.78 |
| G-11 | 0.8 mg/kg | 0.94 ± 0.77** | 7.55 ± 4.28 |
| G-12 | 0.8 mg/kg | 1.01 ± 0.55** | 5.48 ± 4.39 |
| G-22 | 0.8 mg/kg | 0.92 ± 0.28** | 8.81 ± 6.44* |
| G-CSF | 40 μg/kg | 0.63 ± 0.20* | 9.70 ± 5.28** |

Note:
Compared with the model control group between groups,
*P < 0.05,
**P < 0.01;

TABLE 4

Effect of ursolic acid saponin and oleanolic acid saponin on platelets of animal model of CY-induced leukopenia in mice

| Group | Dosage (/kg) | Day 1 after modelng Statistics | Day 5 after modeling Statistics |
|---|---|---|---|
| negative control group | — | 742.30 ± 199.09**★★ | 678.30 ± 178.03**★★ |
| model control group | — | 388.14 ± 116.19 | 176.50 ± 115.24 |
| G-1 | 0.8 mg/kg | 504.67 ± 117.81** | 413.00 ± 218.95*★★ |
| G-3 | 0.8 mg/kg | 473.12 ± 144.68* | 341.93 ± 186.39**★ |
| G-11 | 0.8 mg/kg | 465.00 ± 99.28* | 385.73 ± 198.30**★ |

TABLE 4-continued

Effect of ursolic acid saponin and oleanolic acid saponin on platelets of animal model of CY-induced leukopenia in mice

| Group | Dosage (/kg) | Day 1 after modelng Statistics | Day 5 after modeling Statistics |
|---|---|---|---|
| G-12 | 0.8 mg/kg | 456.88 ± 77.20* | 390.86 ± 203.71**★★ |
| G-22 | 0.8 mg/kg | 491.36 ± 126.28* | 210.00 ± 119.38 |
| G-CSF | 40 μg/kg | 408.38 ± 86.38 | 206.64 ± 140.14 |

Note:
Compared with the model control group between groups,
*P < 0.05,
**P < 0.01,
Δ stands for a good trend.
Compared with G-22 between groups,
★P < 0.05,
★★<0.01.

As can be seen from Table 3 and Table 4 showing the results of Experiment 3, G-1 of ursolic acid saponin has an obvious effect in increasing leukocytes and platelets. There is a significant difference in increasing leukocytes and platelets between G-1, G-3 of ursolic acid saponin and G-22 on day 5 after modeling. G-11 and G-12 of oleanolic acid saponin have an obvious effect in increasing leukocytes at day 1 after modeling, thereby having a certain effect in increasing leukocytes. The effect in increasing platelets is obvious on day 1 and day 5, and there is a significant difference on day 5 compared with G-22. The positive drug G-CSF has no obvious effect in increasing platelets.

Experimental Example 4

In order to illustrate the present invention in detail, with a model induced by $^{60}$Co-γ rays, the effects of G-1 and G-22 on leukocytes of chemotherapy-induced-leukopenia mice were compared. The specific operation and the results are as follows. The dosage regimen is shown in the following table.

TABLE 5

Drug dosage regimen

| Animal | Group | Test Material | Drug Concentration (mg/ml) | Drug Volume (ml/kg) | Drug Dosage (mg/kg) | Administration Route | Administration Time(day) |
|---|---|---|---|---|---|---|---|
| Mice | normal control group | 0.9% physiological saline | / | 20 | / | i.g | 21 |
| | model group | 0.9% physiological saline | / | 20 | / | i.g | 21 |
| | G-1 | G-1 | 0.04 | 20 | 0.80 | i.g | 21 |
| | G-22 | G-22 | 0.04 | 20 | 0.80 | i.g | 21 |
| | positive (G-CSF) | G-CSF | 4 μg/ml | 10 | 40 μg/kg | s.c | day 5 after irradiation |

Experimental Methods and Results:

Healthy Kunming mice, of which half were male and the other half were female, were divided into 6 groups randomly, with 17-18 in each group. Blood was taken from caudal vein to determine the normal hemogram (leucocyte, erythrocyte, platelet and hemoglobin), and adjustments were made according to body weights and hemogram results. The drugs were adminstrated at a dosage ig as shown in Table 5. The normal control group and model group were given isometric physiological saline once a day for 7 days, and then the post-radiation hemogram was determined. Except the normal control group, other groups were each subjected to a whole body exposure to $^{60}$Co-γ rays at a total dose of 3.0 Gy to prepare the models of leukopenia in mice, followed by further administration for 14 days. The G-CSF group was administrated through subcutaneous injection for 5 days from the irradiation day on and the hemogram was determined by taking blood respectively on day 3, day 7 and day 14 after irradiation. The specific results are shown in the following table:

TABLE 6

The effect of test drug on WBC of mice model of $^{60}$Co-γ-induced leukopenia (109/L)

| Group | Dosage (mg/kg) | Number | Normal | Detection Time Point | | | |
|---|---|---|---|---|---|---|---|
| | | | | 1 week after administration | Day 3 after irradiation | Day 7 after irradiation | Day 14 after irradiation |
| Normal Group | / | 17 | 8.51 ± 1.88 | 10.08 ± 2.89 | 10.71 ± 3.63 | 12.30 ± 3.67 | 11.35 ± 3.92 |
| Model Group | / | 18 | 8.47 ± 2.37 | 10.03 ± 2.32 | 2.48 ± 0.97$^{ΔΔ}$ | 3.45 ± 1.13$^{ΔΔ}$ | 5.06 ± 1.08$^{ΔΔ}$ |
| G-1 | 0.80 | 17 | 8.96 ± 1.58 | 9.21 ± 2.16 | 2.06 ± 0.75 | 4.59 ± 1.52** | 6.37 ± 1.54** |
| G-22 | 0.80 | 17 | 8.56 ± 2.43 | 9.50 ± 3.17 | 2.21 ± 0.92 | 4.08 ± 1.50 | 5.44 ± 1.13 |
| G-CSF | 40 μg | 18 | 8.64 ± 2.01 | 9.89 ± 3.30 | 3.71 ± 1.11** | 4.56 ± 1.17** | 7.01 ± 1.52** |

(Compared with normal group, $^{ΔΔ}P < 0.01$; $^{Δ}P < 0.05$; Compared with model group, **$P < 0.01$, *$P < 0.05$.)

Table 6 shows: significantly different from the normal group, the peripheral blood WBC of model mice was decreased obviously on day 3, day 7 and day 14 after irradiation; and after gastric perfusion in the G-1 group, the leucocyte count of the leukopenia mice was increased obviously, and there is a significant difference compared to the model group on day 7 and day 14 after irradiation, whereas G-22 has no evident effect.

Experimental Example 5

Comparison of Hemolytic Activities

The test samples were dissolved in DMSO/physiological saline (1:4) as a solvent to generate the tested concentration gradients of 40, 80, 120, 160, 200 μg/ml. Blood (25 ml) was taken from a rabbit heart, poured into an erlenmeyer flask containing glass beads and shook gently for 10 min to remove fibrinogen so as to convert the blood into defidrinated blood. The resultant blood was transferred into a graduation centrifugal tube. About 10 times physiological saline was added, shook up and centrifuged at 2000 r/min for 5 minutes. The supernatant was removed, and the precipitated erythrocytes were washed with physiological saline again by the above method for 4 times until the supernatant was colorless and transparent. The resultant erythrocytes were prepared into a 10% suspension using physiological saline for testing. 250 μl of the 10% erythrocyte suspension was added into 2.5 ml of a tested sample, solvent (blank control) or distilled water (positive control), mixed thoroughly, and immediately placed in a thermotank maintained at 37° C. for incubation; and it was taken out 1 hour later and centrifuged at 3000 r/min for 5 minutes. The supernatant was taken for determining the OD value at 540 nm with a spectrophotometer. Hemolysis (Hemolysis Percentage)=(absorbance of sample−absorbance of blank control)×100%÷(absorbance of positive control−absorbance of blank control); and the data processing was performed by SPSS13.0 statistical software with drug concentration as an independent variable X and hemolysis as a dependent variable Y to obtain a linear regression equation; then, the drug concentration causing 50% hemolysis, i.e $HD_{50}$, was calculated according to the equation. A P-value <0.05 was considered statistically significant.

TABLE 7

Regression equation and $HD_{50}$ of G series samples

| Samole No. | Determination Coefficient | F | P | Regression Equation (y-hemolysis, x-drug concentration) | $HD_{50}$ (μg/ml) |
|---|---|---|---|---|---|
| G-1 | 0.822 | 13.844 | 0.034 | y = 9.290 + 0.118x | 345 |
| G-3 | 0.928 | 38.856 | 0.008 | y = −30.861 + 0.586x | 137.99 |
| G-6 | 0.857 | 17.939 | 0.024 | y = −28.305 + 0.645x | 121.40 |
| G-8 | 0.889 | 23.961 | 0.016 | y = −12.054 + 0.887x | 69.96 |

It can be seen from the above table that G-1 has the highest $HD_{50}$, showing that among the several samples, G-1 is the most difficult to cause hemolysis, thus being preferably selected.

It is demonstrated by the above pharmacological tests that the compounds according to the present invention not only have an effect in obviously increasing leucocytes and/or platelets, but also have a stronger pharmacological acitivity and a significant difference compared with the pomolic acid saponin isolated from the traditional Chinese medicine-sanguisorba. The efficacy of bisglycosyl ursolic acid saponin G1 is particularly optimal. It is known from the hemolysis test that bisglycosyl ursolic acid saponin G1 among the compounds of the present invention has the highest value of $HD_{50}$ and a high safety; and based on the results of tests regarding efficacy and safety, bisglycosyl ursolic acid saponin G1 is the best choice of the compounds according to the present invention.

Preparation of a Pharmaceutical Composition of the Present Invention

Tablet:

| Compostion: | Amount (mg/tablet) |
|---|---|
| G-1 | 5 |
| starch | 50 |
| microcrystalline cellulose | 40 |
| magnesium stearate | 2 |
| sodium carboxymethylcellulose | 5 |

G-1, starch, microcrystalline cellulose and sodium carboxymethylcellulose were mixed thoroughly according to the above ratio, wetted with water, granulated, dried and pelletized, prior to the addition of magnesium stearate. The mixture was mixed thoroughly and subjected to tabletting to obtain a tablet.

Injection:

50 mg of G-12 was weighed, dissolved in a proper amount of anhydrous ethyl alcohol, and added with 1 g of polyoxyethylene castor oil ester to dissolve it completely. A glucose injection was added to dilute the solution to 100 ml, and 0.05% activited carbon for injection was added, then the temperature was kept at 80° C. for 15 minutes. The mixture was filtered by sintered glass and millipore membrane filters. The filtrate was subpackaged into 2 ml ampoules. Each preparation unit comprises 1 mg of G-12.

Capsule:

10 g of G-6 and 400 g of microcrystalline cellulose were mixed thoroughly and filled into 2,000 No. 1 capsules. Each preparation unit comprises 5 mg of G-6.

Industrial Applicability

The present invention utilizes the cheap and accessible ursolic acid and oleanolic acid which are widely present in natural plants as raw materials, introduces hydrophilic groups, i.e monosaccharyls or oligosaccharyls, by structural modification, and discovers that the resulting saponins not only can improve the water solubility of the parent nucleus, but also have an activity of remarkably increasing leucocytes and/or platelets, as demonstrated by pharmacological tests. Compared to pomolic acid saponin isolated from sanguisorba, they not only have a stronger pharmacological activity, but also have the advantages of simple synthesis, adaptation to industrial production, low cost and so on.

The invention claimed is:

1. A method for increasing the number of leucocytes or platelets in a subject in need thereof, the method comprising administering to the subject an effective amount of 3-O-($\alpha$-L-arabopyranosyl) ursolic acid-28-O-($\alpha$-L-arabopyranosyl) ester.

2. A method for increasing the number of leucocytes or platelets in a subject in need thereof, the method comprising administering to the subject an effective amount of 3-O-($\alpha$-L-arabopyranosyl) oleanolic acid-28-O-($\alpha$-L-arabopyranosyl) ester or 3-O-($\beta$-D-glucopyranosyl) oleanolic acid-28-O-($\beta$-D-glucopyranosyl) ester.

* * * * *